United States Patent
Bardinelli et al.

(12)

(10) Patent No.: US 8,084,482 B2
(45) Date of Patent: Dec. 27, 2011

(54) COMPOSITIONS AND KITS COMPRISING A FUNGICIDAL TRIAZOLE AND AN ALKOXYLATED ALCOHOL, AND THEIR USES

(75) Inventors: Ted R. Bardinelli, Durham, NC (US); Charles W. Finch, Garner, NC (US)

(73) Assignee: BASF SE, Ludwigshafen (DE)

( * ) Notice: Subject to any disclaimer, the term of this patent is extended or adjusted under 35 U.S.C. 154(b) by 424 days.

(21) Appl. No.: 12/517,915

(22) PCT Filed: Dec. 6, 2007

(86) PCT No.: PCT/EP2007/063417
§ 371 (c)(1),
(2), (4) Date: Jun. 5, 2009

(87) PCT Pub. No.: WO2008/068307
PCT Pub. Date: Jun. 12, 2008

(65) Prior Publication Data
US 2010/0323888 A1    Dec. 23, 2010

Related U.S. Application Data

(60) Provisional application No. 60/869,030, filed on Dec. 7, 2006.

(51) Int. Cl.
*A01N 43/647*    (2006.01)
*A01N 43/653*    (2006.01)
*A01N 25/32*    (2006.01)
*A01N 25/30*    (2006.01)
*A01P 3/00*    (2006.01)

(52) U.S. Cl. .......... 514/383; 514/63; 514/359; 514/384; 514/772; 514/922; 514/946; 514/974; 504/103

(58) Field of Classification Search .............. 514/63, 514/359, 383, 384, 772, 922, 946, 974; 504/103
See application file for complete search history.

(56) References Cited

U.S. PATENT DOCUMENTS

| | | | |
|---|---|---|---|
| 4,426,524 | A | 1/1984 | Plummer |
| 4,452,625 | A | 6/1984 | Lürssen et al. |
| 4,532,341 | A | 7/1985 | Holmwood et al. |
| 5,393,770 | A | 2/1995 | Grayson |
| 5,434,313 | A | 7/1995 | Harrison et al. |
| 5,661,121 | A | 8/1997 | Dahlgren et al. |
| 5,968,964 | A | 10/1999 | Rehnig et al. |
| 6,413,908 | B1 | 7/2002 | Reekmans et al. |
| 2004/0110960 | A1 | 6/2004 | Ahlers et al. |
| 2005/0170968 | A1 | 8/2005 | Berghaus et al. |
| 2008/0064756 | A1 | 3/2008 | Berghaus et al. |

FOREIGN PATENT DOCUMENTS

| | | |
|---|---|---|
| DE | 195 20 935 A1 | 12/1996 |
| EP | 0 040 345 A1 | 11/1981 |
| EP | 0 057 357 A2 | 8/1982 |
| EP | 0 155 508 A1 | 9/1985 |
| EP | 0 213 639 A2 | 3/1987 |
| EP | 0 366 089 A2 | 5/1990 |
| EP | 0 970 610 A1 | 1/2000 |
| EP | 1 023 837 A2 | 8/2000 |
| WO | WO-98/35553 A1 | 8/1998 |
| WO | WO 00/42847 A1 | 7/2000 |
| WO | WO 02/15697 A2 | 2/2002 |
| WO | WO 02/083695 A1 | 10/2002 |
| WO | WO-03/090531 A1 | 11/2003 |
| WO | WO 2005/015998 A1 | 2/2005 |
| ZA | 964833 A | 1/1997 |

OTHER PUBLICATIONS

CABA Abstract 2004:150884 (2004).*

* cited by examiner

*Primary Examiner* — John Pak
(74) *Attorney, Agent, or Firm* — Birch, Stewart, Kolasch & Birch, LLP

(57) ABSTRACT

The present invention relates to compositions comprising (a1) a fungicidal triazole; and (b1) ethoxylated 2-propylheptanol having a mole average degree of ethoxylation from 7.5 to 8.5, to kits comprising the triazole and alcohol alkoxylate in separate containers, as well as to their uses in the agricultural field. The present invention also relates to use of ethoxylated 2-propylheptanol having a degree of ethoxylation from 7.5 to 8.5 as adjuvant and surfactant safener.

24 Claims, No Drawings

COMPOSITIONS AND KITS COMPRISING A FUNGICIDAL TRIAZOLE AND AN ALKOXYLATED ALCOHOL, AND THEIR USES

This application is a 371 of PCT/EP2007/063417, filed on Dec. 16, 2007, which claims benefit of U.S. Provisional Application 60/869,030, filed on Dec. 7, 2006.

The present invention relates to compositions comprising a fungicidal triazole and an alcohol alkoxylate, to kits comprising the triazole and alcohol alkoxylate in separate containers, as well as to their uses in the agricultural field. The present invention also relates to the use of ethoxylated 2-propylheptanol having a degree of ethoxylation from 7.5 to 8.5.

In addition to the optimization of the active compound properties, the development of an effective composition is of particular importance with a view to industrial production and application of these active compounds. An optimum balance between properties, such as the biological activity, the toxicology, possible effects on the environment and the costs, which are to some extent conflicting, has to be found through proper formulating of the active compound or compounds. In addition, the formulating determines to a considerable extent the stability and the ease of application of the composition.

The addition to formulations of certain auxiliaries in order to improve the activity is generally known and agricultural practice. The active compound amounts in the formulation can thereby advantageously be reduced while maintaining the activity, which minimizes costs, and, if appropriate, current statutory regulations can be adhered to. In individual cases, success is also achieved in expanding the spectrum of action, as plants which, without additive, can only be treated inadequately with a certain active compound can be appropriately treated by addition of certain auxiliaries. In addition, the performance under unsuitable environmental conditions can in individual cases be enhanced by a suitable formulation. Consequently, incompatibilities between various active compounds in a formulation can also be avoided.

Such auxiliaries are occasionally also described as adjuvants. They are often surface-active or saline compounds. Depending on the mode of action, modifiers, actuators, fertilizers and pH buffers, for example, can be distinguished. Modifiers influence the wetting, adhesion and spreading of a formulation. Actuators break open the waxy cuticle of plants and improve the penetration of the active compound into the cuticle, both in the short term (within minutes) and in the long term (within hours). Fertilizers such as ammonium sulfate, ammonium nitrate or urea improve the absorption and solubility of the active compound and they may reduce antagonistic ways of behavior of active compounds. pH buffers are conventionally used for optimum adjustment of the pH of the formulation.

With regard to the uptake of the active compound in the leaf, surface-active substances may act as modifiers and actuators. It is generally assumed that suitable surface-active substances can increase the effective contact area of liquids on leaves by reducing the surface tension. In addition, certain surface-active substances can dissolve or break open the epicuticular waxes, which facilitates the absorption of the active compound. Furthermore, some surface-active substances can also improve the solubility of active compounds in formulations and therefore prevent, or at least delay, crystallization. Finally, they can in certain cases also influence the absorption of active compounds by retaining moisture.

Adjuvants of surface-active type are used in a variety of ways for agrotechnical applications. They can be subdivided into anionic, cationic, nonionic or amphoteric groups of substances.

Petroleum-based oils are conventionally used as activating adjuvants. More recently, seed extracts, natural oils and their derivatives, for example from soya bean, sunflower and coconut, have also been used.

Synthetic surface-active substances, which are generally used as actuators, are inter alia polyoxyethylene condensates with alcohols, alkylphenols or alkylamines which exhibit HLB values in the range from 8 to 13. In this context, WO 00/42847 mentions, for example, the use of certain linear alcohol alkoxylates in order to increase the activity of agrotechnical biocidal formulations. WO 02/15697 (CA 2,420,217) likewise discloses the use of alcohol alkoxylates as adjuvants in the formulation of triazolopyrimidines.

WO 03/090531 (CA 2,482,758) describes the use of alkoxylated 2-propylheptanols as adjuvant in the treatment of plants. In particular, 2-propylheptanol×7 EO is shown to improve the herbizidal efficacy of bentazone and tritosulfuron formulations.

WO 2005/015998 (CA 2,535,176) describes the use of alkoxylated 2-propylheptanols as adjuvant for funcizidal benzamidoxime derivatives.

Triazols are an important class of active ingredients in the pesticide field. As ergosterol biosynthesis inhibitors, they are primarily employed as fungicides (see, for example, DE 195 20 935 A1 (AU 6124496)). In addition, various of the triazols, which, as such have fungicidal activity, are occasionally also described as having plant-growth regulatory properties (see, for example, EP 0 040 345 A2 (CA 1,341,521); EP 0 057 357 A2 (CA 1,177,660)).

Application of said triazoles to plants may cause leave damage. For instance, in soybeans brown spots that appear within 48 hours after triazole application suggest a necrotic damage of the leave. Further, chlorosis (a kind of a bleaching effect on the leave) in susceptible varieties may develop nearly a month after application. For instance, in soybeans chlorosis is accompanied by a bleaching effect that appears 21 to 28 days after triazole application. Depending on the extent of chlorosis, the plant may completely recover or the chlorosis may deteriorate in subsequent necrosis with significant leave damage.

In U.S. Pat. No. 5,393,770 and EP-A-0 970 610 (U.S. Pat. No. 5,968,964), liquid compositions comprising a fungicidal triazole are described. In order to reduce the phytotoxicity that is observed when such liquid compositions are applied in high dose rates and in a short intervall EP-A-0 970 610 teaches to use a mixture of 2-methylbutanol and 1-pentanol as carrier wherein the ratio of the 1-pentanol to the 2-methylbutanol is from 1:1 to 1:10.

It has now been observed that the use of certain alcohol alkoxylates in combination with fungicidal triazoles generally increases the occurrence of chlorosis. For instance, Neodol® 91-6 (a $C_9$-$C_{11}$ alcohol×6 EO) which is used as solubilizing agent in the compositions described in EP-A-0 970 610 causes significant chlorosis when applied to soybeans.

It was thus an object to provide means for applying fungicidal triazoles so as to exert good fungicidal activity while keeping the degree of phytotoxicity acceptable.

It has now been found that fungicidal triazoles, when applied in combination with ethoxylated 2-propylheptanols having an ethoxylation degree of around 8, exhibit a particularly good fungicidal activity without causing too much plant damage.

The fungicidal triazoles and the ethoxylated 2-propylheptanols can be applied in combination as ingedients of a common composition or separately.

The present invention therefore relates to compositions comprising (a1) a fungicidal triazole; and (b1) ethoxylated 2-propylheptanol having a mole average degree of ethoxylation from 7.5 to 8.5.

The present invention therefore also relates to kits having at least two containers, in which (a) a first container comprises a fungicidal triazole; and (b) a second container comprises ethoxylated 2-propylheptanol having a mole average degree of ethoxylation from 7.5 to 8.5.

Alkoxylated 2-propylheptanols are known per se. For example, U.S. Pat. No. 5,661,121, WO 03/09053 and, WO 2005/015998 all describe alkoxylated 2-propylheptanols. Generally, these are obtainable by alkoxylating 2-propylheptanol.

2-Propylheptanols are also referred to as Guerbet alcohols. These can be obtained, for example, by dimerization of the corresponding primary alcohols at elevated temperature, for example 180 to 300° C., in the presence of an alkaline condensing agent, such as potassium hydroxide.

Further, suitable educts for preparing 2-popylheptanol include a number of hydrocarbon sources, e.g., 1-butene, 2-butene, raffinate I—an alkan/alkene mixture obtained from the $C_4$-fraction of a cracker after having separated acetylene and dienes, which further comprises significant amounts of isobutene—or raffinate II, which is obtained from raffinate I by complete or essentially complete separation of isobutene. Of course, mixtures of raffinat I and raffinat II can also be used as educt. These olefines or olefine mixtures can be hydroformylated using known cobalt or rhodium catalysts whereby a mixture of n- and iso-valeraldehyde is formed from 1-butene, the term iso-valeraldehyde designating 2-methylbutanal. The n/iso-ratio of the resulting mixture varies depending on the catalyst and conditions employed (see, for instance, EP-A 155 508, EP-A 213 639, WO 02/83695).

The resulting mixture of $C_5$-aldehydes or a purified fraction thereof can then be subjected to aldol condensation. The aldol condensation is carried out using a basic catalyst, such as sodium or potassium hydroxide, for instance in accordance with the processes described in EP-A 366 089, U.S. Pat. No. 4,426,524 or U.S. Pat. No. 5,434,313. n-Valeraldehyde is converted to 2-propylheptenal. Mixtures of isomeric $C_5$-aldehydes yield a mixture of isomeric products from the homoaldol condensation of identical aldehyde molecules and the crossed aldol condensation of different isomers. The resulting aldol condensation products can then be hydrogenated using conventional catalysts, which yields the corresponding alcohols or alcohol mixtures.

Suitable mixtures of 2-propylheptanol with propylheptanol isomers for producing ethoxylated 2-propylheptanols of the present invention include, for instance, those having:

a) 60 to 98% by weight 2-propylheptanol, 1 to 15% by weight 2-propyl-4-methyl-hexanol and 0.01 to 20% by weight 2-propyl-5-methyl-hexanol and 0.01 to 24% by weight 2-isopropylheptanol;

b) 75 to 95% by weight 2-propylheptanol, 2 to 15% by weight 2-propyl-4-methyl-hexanol, 1 to 20% by weight 2-propyl-5-methyl-hexanol, 0.1 to 4% by weight 2-isopropylheptanol, 0.1 to 2% by weight 2-isopropyl-4-methylhexanol and 0.1 to 2% by weight 2-isopropyl-5-methyl-hexanol;

c) 85 to 95% by weight 2-propylheptanol, 6 to 12% by weight 2-propyl-4-methyl-hexanol and 0.1 to 2% by weight 2-propyl-5-methyl-hexanol and 0.01 to 1% by weight 2-isopropylheptanol; or d) 80 to 92% by weight 2-propylheptanol, 6 to 12% by weight 2-propyl-4-methyl-hexanol, 7 to 13% by weight 2-propyl-5-methyl-hexanol, 0.1 to 2% by weight 2-isopropylheptanol, 0.1 to 1% by weight 2-isopropyl-4-methyl-hexanol and 0.1 to 1% by weight 2-isopropyl-5-methyl-hexanol;

the sum of the components not exceeding 100% by weight. Preferably, the proportions of said components amount to 100% by weight.

Ethoxylated 2-propylheptanols which are suitable according to the present invention are in particular obtainable by ethoxylating either essentially pure 2-propylheptanol or an alcohol mixture which comprise 2-propylheptanol as main component and one or more than one of its isomers, i.e., 2-propyl-4-methyl-hexanol, 2-propyl-5-methyl-hexanol, 2-isopropyl-heptanol, 2-isopropyl-4-methyl-hexanol, 2-isopropyl-5-methyl-hexanol and/or 2-propyl-4,4-dimethylpentanol, e.g., as defined above.

The ethoxylates can generally be obtained by addition of ethylene oxide to the alchol or alcohol mixture and usually comprise a mixture of ethoxylates having varying amounts of ethylene oxide units per molecule. The mole average degree of ethoxylation (i.e., the mean molar ratio of ethylene oxide units ($C_2H_5O$) per mole of alcohol and thus per molecule; also referred to as mole average ethoxylation number), the range of ethoxylation (i.e. the range between the minimum and the maximum ethoxylation number), and the proportion of each particular ethoxylate obtained (weight percent distribution of the homologues of ethoxylates obtained) depends on the amount of ethylene oxide added per mole of alcohol and on the reaction conditions employed.

Preference is given to ethoxylated 2-propylheptanols having a mean molar ratio of ethylene oxide units per 2-propylheptyl unit (mole average degree of ethoxylation; mole average ethoxylation number) of approximately 7.5 to 8.5, of approximately 7.7 to 8.3, of approximately 7.9 to 8.1, of approximately 7.95 to 8.05 or of about 8 ethylene oxide per mole of 2-propylheptanol.

Ethoxylates with a Poisson-like homologue distribution are preferred according to the present invention. Such a Poisson-like homologue distribution has one maximum.

Ethoxylates with a narrow, Poisson-like homologue distribution, so-called narrow range ethoxylates (NRE), are especially preferred according to the present invention. Such NREs include in particular ethoxylates wherein at least about 70% by weight, at least about 80% by weight or at least about 90% by weight of the exthoxylated 2-propylheptanols have an ethoxylation number between 6 and 10, between 7 and 9, or between 7.5 and 8.5.

Preference is also given to ethoxylated 2-propylheptanols wherein the proportion of ethoxylated 2-propylheptanol having a molar ratio of 8 ethylene oxide units per molecule, i.e. ethoxylated 2-propylheptanol of the formula (I)

$$R\text{—}O\text{—}(C_2H_4O)_x\text{—}H \qquad (I)$$

wherein R is 2-propylheptyl and x is 8, is at least 50% by weight, least 60% by weight, least 70% by weight, least 80% by weight, least 90% by weight or at least 95% by weight based on the total weight of ethoxylated 2-propylheptanol.

High temperature gas chromatography (HT-GC) coupled to atomic emission detection (AED) can be used for the determination of alkyl chain distribution, mole average degree of ethoxylation and weight percent distribution of the corresponding homologues of alcohol ethoxylates even without all the actual homologues being available as pure references (the ASTM method "standardtest methods for chemical analysis of alcohol ethoxylates and alkylphenol ethoxylates" has the designation D 4252-89). The product specifications can quickly be checked by determining the cloud point (DIN 53971).

The reaction of the 2-propylheptanol or 2-propylheptanol mixtures with the ethylene oxide can be carried out according to conventional processes known to a person skilled in the art and in conventional apparatuses therefor.

It can be catalyzed by strong bases, such as alkali metal hydroxides and alkaline earth metal hydroxides, Brönsted acids or Lewis acids, such as $AlCl_3$, $BF_3$, and the like. Catalysts such as hydrotalcite or DMC can be used for alcohol ethoxylates with a narrow distribution.

The ethoxylation is preferably carried out at temperatures ranging from approximately 80 to 250° C., preferably approximately 100 to 220° C. The pressure is preferably between ambient pressure and 600 bar. If desired, the ethylene oxide can comprise an admixture of inert gas, e.g. from approximately 5 to 60%.

Assuming the same acidity of the starting 2-propyheptanol and all (oligo)glycol ethers of 2-propylheptanol present in the reaction mixture, a Poisson distribution of the individual species can be expected in the ethoxylation, with a maximum corresponding to that oligoglycol ether in which the number of added ethylene oxide units corresponds to the molar ratio of ethylene oxide to starting 2-propylheptanol. However, on account of different acidities of the individual species in the reaction mixture the homologue distribution that is actually observed in the ethoxylation mixture usually differs from the Poisson distribution.

This is true for all alkaline catalysts, although the deviations in the case of alkaline-earth compounds are less strongly pronounced than in the case of sodium hydroxide or sodium methoxide. The distribution pattern of the homologous polyethylene glycol ethers in an ethoxylate obtained by alkaline catalysis is independent of the temperature, pressure, and catalyst concentration.

When Lewis acids such boron trifluoride, tin tetrachloride, or antimony pentachloride are used as catalysts, homologue distributions approximating to the Poisson distribution are obtained, because here it is not the proton activity but the nucleophilicity of the substrate that determines the reaction pathway. Lewis acids activate ethylene oxide and not the alcohol.

However, Lewis acids have not become established as catalysts since they must be laboriously removed from the reaction product and because they lead to the formation of polyethylene glycol [the so-called polydiol, $HO(CH_2CH_2O)_nH$], methyldioxolane and dioxane, due to side reactions and decomposition reactions.

Recent emphasis has been on the development of amphoteric catalysts that give distributions similar to those produced by Lewis acids. Among these catalysts a calcined hydrotalcite of idealized empirical formula $Mg_6Al_2O_5(OH)_2$ is of interest since it can readily be handled as a pneumatically conveyable powder and can easily be separated as an insoluble solid from the reaction medium.

The term "fugicidal triazole" refers to active ingredients from the triazole class which have suitable fungicidal activity. Triazoles, their preparation and their action against harmful fungi are generally known (cf.: http://www.alanwood.net/pesticides/); they are commercially available. Example of triazoles include:

Azaconazol 1-[[2-(2,4-dichlorophenyl)-1,3-dioxolan-2-yl]methyl]-1H-1,2,4-triazol CAS RN [50207-31-0];

bitertanol, β-([1,1'-biphenyl]-4-yloxy)-α-(1,1-dimethylethyl)-1H-1,2,4-triazole-1-ethanol (DE 23 24 020), bromuconazole, 1-[[4-bromo-2-(2,4-dichlorophenyl)tetrahydro-2-furanyl]methyl]-1H-1,2,4-triazole (Proc. 1990 Br. Crop. Prot. Conf.—Pests Dis. Vol. 1, p. 459), cyproconazole, 2-(4-chlorophenyl)-3-cyclopropyl-1-[1,2,4]triazol-1-ylbutan-2-ol (U.S. Pat. No. 4,664,696);

difenoconazole, 1-{2-[2-chloro-4-(4-chlorophenoxy)phenyl]-4-methyl-[1,3]dioxolan-2-ylmethyl}-1H-[1,2,4]triazole (GB-A 2 098 607);

diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575), enilconazole (imazalil), 1-[2-(2,4-dichlorophenyl)-2-(2-propenyloxy)ethyl]-1H-imidazole (Fruits, 1973, Vol. 28, p. 545);

epoxiconazole, (2RS,3SR)-1-[3-(2-chlorophenyl)-2,3-epoxy-2-(4-fluorophenyl)propyl]-1H-1,2,4-triazole (EP-A 196 038);

fluquinconazole, 3-(2,4-dichlorophenyl)-6-fluoro-2-[1,2,4]triazol-1-yl-3H-quinazolin-4-one (Proc. Br. Crop Prot. Conf.—Pests Dis., 5-3, 411 (1992));

fenbuconazole, α-[2-(4-chlorophenyl)ethyl]-α-phenyl-1H-1,2,4-triazole-1-propanenitrile (Proc. 1988 Br. Crop Prot. Conf.—Pests Dis. Vol. 1, p. 33), flusilazole, 1-{[bis-(4-fluorophenyl)methylsilanyl]methyl}-1H-[1,2,4]triazole (Proc. Br. Crop Prot. Conf.—Pests Dis., 1, 413 (1984));

flutriafol, α-(2-fluorophenyl)-α-(4-fluorophenyl)-1H-1,2,4-triazole-1-ethanol (EP 15 756), hexaconazole, 2-(2,4-dichlorophenyl)-1-[1,2,4]triazol-1-ylhexan-2-ol [CAS-RN 79983-71-4];

imibenconazole, (4-chlorophenyl)methyl N-(2,4-dichlorophenyl)-1H-1,2,4-triazole-1-ethaneimidothioate (Proc. 1988 Br. Crop Prot. Conf.—Pests Dis. Vol. 2, p. 519), ipconazole, 2-[(4-chlorophenyl)methyl]-5-(1-methylethyl)-1-(1H-1,2,4-triazol-1-yl-methyl)cyclopentanol (EP 267 778), metconazole, 5-(4-chlorobenzyl)-2,2-dimethyl-1-[1,2,4]triazol-1-ylmethylcyclopentanol (GB 857 383);

myclobutanil, 2-(4-chlorophenyl)-2-[1,2,4]triazol-1-ylmethylpentanenitrile [CAS RN 88671-89-0];

paclobutrazole, (2RS,3RS)-1-(4-chlorophenyl)-4,4-dimethyl-2-(1H-1,2,4-triazole-1-yl)pentan-3-ol [CAS RN 76738-62-0];

penconazole, 1-[2-(2,4-dichlorophenyl)pentyl]-1H-[1,2,4]triazole (Pesticide Manual, 12th Ed. (2000), page 712);

propiconazole, 1-[[2-(2,4-dichlorophenyl)-4-propyl-1,3-dioxolan-2-yl]methyl]-1H-1,2,4-triazole (BE 835 579), prothioconazole, 2-[2-(1-chlorocyclopropyl)-3-(2-chlorophenyl)-2-hydroxypropyl]-2,4-dihydro-[1,2,4]triazol-3-thione (WO 96/16048);

simeconazole, α-(4-fluorophenyl)-α-[(trimethylsilyl)methyl]-1H-1,2,4-triazole-1-ethanol [CAS RN 149508-90-7], triadimefon, 1-(4-chlorophenoxy)-3,3-dimethyl-1-(1H-1,2,4-triazol-1-yl)-2-butanone;

triadimenol, β-(4-chlorophenoxy)-α-(1,1-dimethylethyl)-1H-1,2,4-triazole-1-ethanol;

tebuconazole, 1-(4-chlorophenyl)-4,4-dimethyl-3-[1,2,4]triazol-1-ylmethylpentan-3-ol (EP-A 40 345);

tetraconazole, 1-[2-(2,4-dichlorophenyl)-3-(1,1,2,2-tetrafluorethoxy)propyl]-1H-1,2,4-triazole (EP 234 242), triticonazole, (5E)-5-[(4-chlorophenyl)methylene]-2,2-dimethyl-1-(1H-1,2,4-triazol-1-ylmethyl)cyclopentanol (FR 26 41 277);

uniconazole, (E)-(RS)-1-(4-chlorophenyl)-4,4-dimethyl-2-(1H-1,2,4-triazole-1-yl)pent-1-en-3-ol [CAS RN 83657-22-11].

Those which are preferably used, mainly with regard to efficacy and safety in accordance with the invention, are metconazole, triadimenol, triadimefon, cyproconazole, tebuconazole, uniconazole, paclobutrazole, ipconazole, prothioconazole, tetraconazole, epoxiconazole, propionazole, triticonazole, difenoconazole, fenbuconazole, and flusilazole.

Particularly preferred are metconazole, tebuconazole, epoxiconazole, prothioconazole, and cyproconazole.

Owing to the basic character of their nitrogen atoms, said triazoles are capable of forming salts with inorganic or organic acids. Thus, agriculturally utilizable salts of the triazoles can also be employed in accordance with the present invention.

Examples of inorganic acids are hydrohalic acids, such as hydrogen fluoride, hydrogen chloride, hydrogen bromide and hydrogen iodide, carbonic acid, sulphuric acid, phosphoric acid and nitric acid.

Suitable organic acids are, for example, formic acid and alkanoic acids, such as acetic acid, trifluoroacetic acid trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or disulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or diphosphonic acids (aromatic radicals, such as phenyl and naphthyl, which carry one or two phosphoric acid radicals), where the alkyl or aryl radicals may carry further substituents, as in for example p-toluenesulfonic acid, salicylic acid, p-aminosalicylic acid, 2-phenoxybenzoic acid, 2-acetoxybenzoic acid, etc.

Preferred in accordance with the invention is metconazole, of the formula (II):

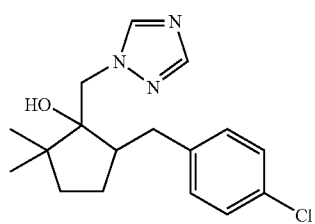

(II)

or an agriculturally utilizable salt thereof.

The representation of metconazole of the formula (II) which has been chosen here includes isomeric forms of these compounds. Those which must be mentioned in particular are stereoisomers, such as enantiomers or diastereoisomers of the formulae (IIa-d). Besides the essentially pure isomers, the compounds of the formulae (II) also include their isomer mixtures, for example stereoisomer mixtures. A high proportion of cis isomers is preferred, advantageously with a cis: trans ratio of 5:1 to 20:1.

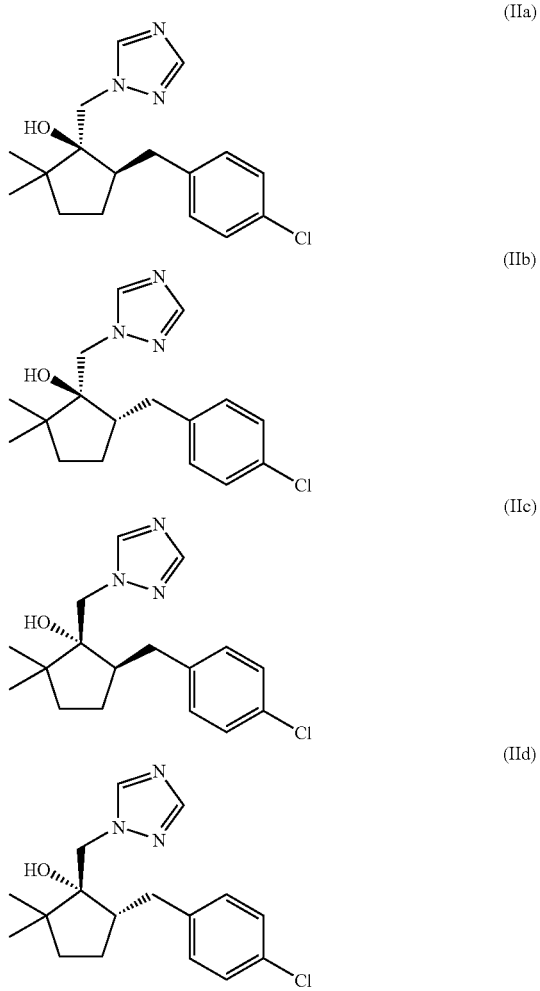

In the present case, the agriculturally utilizable metconazole salts are preferably acid addition salts.

Anions of useful acid addition salts are predominantly chloride, bromide, fluoride, hydrogen sulfate, sulfate, dihydrogen phosphate, hydrogen phosphate, phosphate, nitrate, hexafluorosilicate, hexafluorophosphate.

The fungicidal triazoles can be used together with additional active compounds, e.g. with herbicides, insecticides, growth regulators or fungicides or also with fertilizers.

On mixing with fungicides, an expansion of the fungicidal spectrum of activity is obtained in many cases.

In particular, the fungicidal triazoles can be used together with one or more than one fungicide selected from the group consisiting of strobilurins, such as azoxystrobin, dimoxystrobin, fluoxastrobin, kresoxim-methyl, metominostrobin, oryzastrobin, picoxystrobin, pyraclostrobin and trifloxystrobin, imidazole fungicides auch as fenamidone, and oxazole fungicides such as famoxadone.

More particularly, the present invention also relates to compositions comprsing an active ingredient component (a) which comprises (a1) at least one fungicidal triazole, and an adjuvant component (b) which comprises (b1) at least one ethoxylated 2-propylheptanol, as defined herein. The component (a) may comprise further active ingredients and the component (b) may comprise further adjuvants.

In said compostion, the ratio by weight of the component (b1) to the component (a1) is usually at least 0.5. In order to guarantee a satisfactory adjuvant effect, the ratio by weight of component (b1) to component (a1) is preferably more than 0.5, in particular more than 1 and advantageously more than 2, 5, 10 or 20.

The proportion of the component (a) in respect of the total weight of the composition generally comes to more than 1% by weight, preferably more than 2% by weight and in particular more than 2.5% by weight. On the other hand, the proportion of the component (a) in respect of the total weight of the composition generally comes to less than 75% by weight, preferably less than 60% by weight and in particular less than 50% by weight.

The proportion of the component (a1) in respect of the total weight of the composition generally comes to more than 1% by weight, preferably more than 2% by weight and in particular more than 2.5% by weight. On the other hand, the proportion of the component (a1) in respect of the total weight of the composition generally comes to less than 50% by weight, preferably less than 40% by weight and in particular less than 35% by weight.

According to one embodiment of the present invention, the component (a) essentially consists of (a1), i.e.
(a1) one or more than one fungicial triazole.

According to a particular embodiment, compositions according to the invention comprise, as additional active ingredient:
(a2) at least one or more than one of the combination partners described above, in particular one or more active compounds, which are selected from the strobilurins described above.

The relative proportions of active ingredients in such compositions comprising a combination of active ingredients are highly variable and depend on the active ingredients used.

Proportions of the component (b) in respect of the total weight of the composition of more than 5% by weight, preferably of more than 8% by weight and in particular of more than 10% by weight are advantageous. On the other hand, proportions of the component (b) in respect of the total weight of the composition of less than 80% by weight, preferably of less than 60% by weight and in particular of less than 50% by weight are generally advisable.

Proportions of the component (b1) in respect of the total weight of the composition of more than 5% by weight, preferably of more than 8% by weight, in particular of more than 10% by weight, especially of more than 15% by weight and in particular of more than 20% by weight are advantageous. On the other hand, proportions of the component (b1) in respect of the total weight of the composition of less than 60% by weight, preferably of less than 50% by weight and in particular of less than 40% by weight are generally advisable.

According to one embodiment of the present invention, the adjuvant component (b) essentially consists of (b1), i.e. one or more than one ethoxylated 2-propylheptanol as defined herein.

Compositions according to the invention preferably belong to the group of the liquid formulations. These include in particular water-soluble concentrates (SL formulations), suspension concentrates (SC formulations), suspoemulsions (SE formulations) and microemulsions. According to one embodiment, the compositions of the present invention are dispersible concentrates (DC).

According to a particular embodiment of the present invention, the compositions comprise, as component (c), at least one auxiliary.

The component (c) can serve many different purposes. The choice of suitable auxiliaries is usually made according to requirements by a person skilled in the art.

For example, auxiliaries are chosen from
(c1) surface-active auxiliaries;
(c2) suspension agents, antifoaming agents, retention agents, pH buffers and drift retardants;
(c3) trace elements and minerals which can be used by plants;
(c4) chelating agents;
(c5) solvents or diluents.

The proportion of the component (c) in respect of the total weight of the composition is, if present, generally 10 to 60% by weight, preferably 15 to 50% by weight and in particular 20 to 45% by weight.

The term "surface-active auxiliary" means in this instance interface-active or surface-active agents, such as surfactants, dispersing agents, emulsifying agents or wetting agents.

Anionic, cationic, amphoteric and nonionic surfactants can be used in principle.

The anionic surfactants include, for example, carboxylates, in particular alkali metal, alkaline earth metal and ammonium salts of fatty acids, e.g. potassium stearate, which are usually also described as soaps; acylglutamates; sarcosinates, e.g. sodium lauroylsarcosinate; taurates; methylcelluloses; alkyl phosphates, in particular alkyl monophosphates and alkyl diphosphates; sulfates; sulfonates, in particular alkylsulfonates and alkylarylsulfonates, especially alkali metal, alkaline earth metal and ammonium salts of arylsulfonic acids and alkyl-substituted arylsulfonic acids, alkylbenzenesulfonic acids, such as, for example, lignosulfonic acid and phenolsulfonic acid, naphthalene- and dibutylnaphthalenesulfonic acids, or dodecylbenzenesulfonates, alkylnaphthalenesulfonates, alkyl methyl ester sulfonates, condensation products of sulfonated naphthalene and derivatives thereof with formaldehyde, condensation products of naphthalenesulfonic acids, phenol- and/or phenolsulfonic acids with formaldehyde or with formaldehyde and urea, or monoalkyl or dialkyl sulfosuccinates; and protein hydrolyzates and lignin sulfite waste liquors. The abovementioned sulfonic acids are advantageously used in the form of their neutral or, if appropriate, basic salts.

The cationic surfactants include, for example, quaternary ammonium salts, in particular alkyltrimethylammonium halides, dialkyldimethylammonium halides, alkyltrimethylammonium alkyl sulfates and dialkyldimethylammonium alkyl sulfates, and pyridine and imidazoline derivatives, in particular alkylpyridinium halides.

The nonionic surfactants include in particular:
  alkylaryl alkoxylates, in particular alkylphenol alkoxylates and especially their ethoxylates, such as, for example, ethoxylated isooctylphenol, octylphenol or nonylphenol, tributylphenol polyoxyethylene ether;
  fatty alcohol polyoxyethylene alkyl esters, for example lauryl alcohol polyoxyethylene ether acetate;
  alkoxylated animal and/or vegetable fats and/or oils, for example corn oil ethoxylates, castor oil ethoxylates or tallow fat ethoxylates;
  glycerol esters, such as, for example, glyceryl monostearate,
  fatty amine alkoxylates, fatty acid amide alkoxylates and fatty acid diethanolamide alkoxylates, in particular their ethoxylates;
  sugar surfactants, in particular sorbitol esters, such as, for example, sorbitan fatty acid esters (sorbitan monooleate, sorbitan tristearate), and ethoxylated carboxylic acids and esters of mono- or polyfunctional alcohols, such as polyoxyethylene sorbitan fatty acid esters, alkyl(poly) glycosides and N-alkylgluconamides;

alkyl methyl sulfoxides;

alkyldimethylphosphine oxides, such as, for example, tetradecyldimethylphosphine oxide;

di-, tri- and multiblock polymers of the $(AB)_x$, ABA and BAB type, e.g. polystyrene-block-polyethylene oxide, and AB comb polymers, e.g. polymethacrylate-comb-polyethylene oxide, and in particular ethylene oxide-propylene oxide block copolymers or their end-capped derivatives.

The amphoteric surfactants include, for example, sulfobetaines, carboxybetaines and alkyldimethylamine oxides, e.g. tetradecyldimethylamine oxide.

Additional surfactants which may be mentioned here by way of example are perfluorinated surfactants, silicone surfactants, phospholipids, such as, for example, lecithin or chemically modified lecithins, amino acid surfactants, e.g. N-lauroylglutamate, and surface-active homo- and copolymers, e.g. polyvinylpyrrolidone, polyacrylic acids in the form of their salts, polyvinyl alcohol, polypropylene oxide, polyethylene oxide, maleic anhydride-isobutene copolymers and vinylpyrrolidone-vinyl acetate copolymers.

The proportion of the component (c1) in respect of the total weight of the composition is, if present, generally up to 20% by weight, preferably up to 15% by weight, especially up to 10% by weight and in particular up to 5% by weight.

Suspension agents can be used in particular for suspension concentrates. These are used especially for rheological stabilization. Mention may in particular be made, in this connection, of inorganic products, e.g. bentonites, talcites and hectorites.

The antifoaming agents include in particular those of silicone type, for example the Silicone SL sold by Wacker, and the like.

If present, the proportion of the component (c2) in respect of the total weight of the composition is generally 0.1 to 10% by weight and preferably 0.2 to 5% by weight.

The trace elements and minerals which can be used by plants include in particular inorganic ammonium salts, such as ammonium sulfate, ammonium nitrate, ammonium chloride or ammonium phosphate, or other trace elements or minerals which can be used by plants, in particular ammonium nitrate fertilizer granules and/or urea. These can be introduced into the compositions according to the invention, for example, as aqueous concentrates and, if appropriate, mixed concentrates, such as, e.g., Ensol solutions.

If present, the proportion of the component (c3) in respect of the total weight of the composition is generally 0.1 to 35% by weight and preferably 0.2 to 20% by weight.

Preferred chelating agents are compounds which complex heavy metals and in particular transition metals, e.g. EDTA and its derivatives.

If present, the proportion of the component (c4) in respect of the total weight of the composition is generally 0.001 to 0.5% by weight, preferably 0.005 to 0.2% by weight and in particular 0.01 to 0.1% by weight.

The compositions can comprise solvents of soluble constituents or diluents of insoluble constituents of the composition.

Mineral oils, synthetic oils and vegetable and animal oils, and low-molecular-weight hydrophilic solvents, such as alcohols, ethers, ketones, and the like, for example, can be used in principle.

Mention may therefore first be made especially of aprotic or nonpolar solvents or diluents, such as mineral oil fractions of medium to high boiling point, e.g. kerosene and diesel oil, furthermore coal tar oils, hydrocarbons, paraffin oils, e.g. $C_8$ to $C_{30}$ hydrocarbons of the n-alkane or isoalkane series or mixtures thereof, or optionally hydrogenated or partially hydrogenated aromatics or alkylaromatics from the benzene or naphthalene series, e.g. aromatic or cycloaliphatic $C_7$ to $C_{18}$ hydrocarbon compounds, aliphatic or aromatic carboxylates or dicarboxylates, or fats or oils of vegetable or animal origin, such as mono-, di- or triglycerides, in the pure form or as a mixture, for example in the form of oily extracts of natural substances, e.g. olive oil, soybean oil, sunflower oil, castor oil, sesame oil, corn oil, groundnut oil, rapeseed oil, linseed oil, almond oil, castor oil or safflower oil, and their raffinates, e.g. hydrogenated or partially hydrogenated products thereof, and/or their esters, in particular methyl and ethyl esters.

Examples of $C_8$ to $C_{30}$ hydrocarbons of the n-alkane or isoalkane series are n-octane, n-decane, n-hexadecane, n-octadecane, n-icosane, isooctane, isodecane, isohexadecane, isooctadecane and isoicosane, and preferably hydrocarbon mixtures, such as paraffin oil (which as technical grade can comprise up to approximately 5% of aromatics) and a $C_{18}$-$C_{24}$ mixture which is commercially available from Texaco under the name Spraytex oil.

The aromatic or cycloaliphatic $C_7$ to $C_{18}$ hydrocarbon compounds include in particular aromatic or cycloaliphatic solvents from the alkylaromatics series. These compounds may be nonhydrogenated, partially hydrogenated or completely hydrogenated. Such solvents include in particular mono-, di- or trialkylbenzenes, tetralins substituted by one, two or three alkyl groups and/or naphthalenes substituted by one, two, three or four alkyl groups (alkyl preferably represents $C_1$-$C_6$-alkyl). Examples of such solvents are toluene, o-, m- or p-xylene, ethylbenzene, isopropylbenzene, tert-butylbenzene and mixtures, such as the products sold by Exxon under the Shellsol and Solvesso names, e.g. Solvesso 100, 150 and 200.

Examples of suitable monocarboxylates are oleates, in particular methyl oleate and ethyl oleate, laurates, in particular 2-ethylhexyl laurate, octyl laurate and isopropyl laurate, isopropyl myristate, palmitates, in particular 2-ethylhexyl palmitate and isopropyl palmitate, stearates, in particular n-butyl stearate, and 2-ethylhexyl 2-ethylhexanoate.

Examples of suitable dicarboxylates are adipates, in particular dimethyl adipate, di(n-butyl)adipate, di(n-octyl)adipate, di(isooctyl)adipate, also described as bis(2-ethylhexyl) adipate, di(n-nonyl)adipate, di(isononyl)adipate and ditridecyl adipate; succinates, in particular di(n-octyl)succinate and di(isooctyl)succinate, and di(isononyl)cyclohexane-1,2-dicarboxylate.

The proportion of the aprotic solvents or diluents described above in respect of the total weight of the composition is generally less than 30% by weight, preferably less than 20% by weight and in particular less than 5% by weight.

Mention may secondly be made of protic or polar solvents or diluents, e.g. water, $C_2$-$C_8$ monoalcohols, such as ethanol, propanol, isopropanol, butanol, isobutanol, tert-butanol, 1-pentanol, 2-methylbutanol, cyclohexanol and 2-ethylhexanol, $C_3$-$C_8$ ketones, such as diethyl ketone, t-butyl methyl ketone and cyclohexanone, and aprotic amines, such as N-methylpyrrolidone and N-octylpyrrolidone. According to a particular embodiment of the prensent invention, a mixture of 1-pentanol and 2-methylbutanol is employed. Usually, the ratio of the 1-pentanol to the 2-methylbutanol is from 1:1 to 1:10. Preferably, the ratio is from 1:1 to 1:5, in particular from 49:51 to 40:60.

According to a particular embodiment of the present invention, the proportion of the protic or polar solvents or diluents described above in respect of the total weight of the composition is generally less than 20% by weight, preferably less than 15% by weight and in particular less than 10% by weight.

According to a particular embodiment, the present invention relates to compositions comprising
(a) 2 to 35% by weight of a fungicial triazole, preferably metconazole;
(b) 5 to 60% by weight of ethoxylated 2-propylhepaptanol; and, optionally,
(c) 15 to 45% by weight of one or more than one auxiliary, in particular solvent as described above.

The following are examples of compositions for dilution with water.

A) Water-Soluble Concentrates (SL)

10 parts by weight of the ethoxylated 2-propylhepaptanol and the triazole according to the invention are dissolved in 90 parts by weight of water or of a water-soluble solvent. As an alternative, wetting agents or other auxiliaries are added. The active compound dissolves upon dilution with water.

B) Dispersible Concentrates (DC)

20 parts by weight of the ethoxylated 2-propylhepaptanol and the triazole according to the invention are dissolved in 70 parts by weight of cyclohexanone with addition of 10 parts by weight of dispersant, for example polyvinylpyrrolidone. Dilution with water gives a dispersion.

C) Emulsifiable Concentrates (EC)

15 parts by weight of the ethoxylated 2-propylhepaptanol and the triazole according to the invention are dissolved in 75 parts by weight of xylene with addition of calcium dodecylbenzenesulfonate and castor oil ethoxylate (in each case 5 parts by weight). Dilution with water gives an emulsion.

D) Emulsions (EW, EO)

25 parts by weight of the ethoxylated 2-propylhepaptanol and the triazole according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (e.g. Ultraturrax) and made into a homogeneous emulsion. Dilution with water gives an emulsion.

E) Suspensions (SC, OD)

In an agitated ball mill, 20 parts by weight of the ethoxylated 2-propylhepaptanol and the triazole according to the invention are comminuted with addition of 10 parts by weight of dispersants and wetting agents and 70 parts by weight of water or an organic solvent to give a fine active compound suspension. Dilution with water gives a stable suspension of the active compound.

F) Water-Dispersible Granules and Water-Soluble Granules (WG, SG)

50 parts by weight of the ethoxylated 2-propylhepaptanol and the triazole according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound.

G) Water-Dispersible Powders and Water-Soluble Powders (WP, SP)

75 parts by weight of the ethoxylated 2-propylhepaptanol and the triazole according to the invention are ground in a rotor-stator mill with addition of 25 parts by weight of dispersants, wetting agents and silica gel. Dilution with water gives a stable dispersion or solution of the active compound.

The following is an example of a composition to be applied undiluted.

K) ULV Solutions (UL).

10 parts by weight of the ethoxylated 2-propylhepaptanol and the triazole according to the invention are dissolved in 90 parts by weight of an organic solvent, for example xylene. This gives a product to be applied undiluted having an active compound content of 10% by weight.

Compositions according to the invention can be prepared in a way known per se. For this, at least portions of the components are mixed together. In this connection, it may be observed that products, in particular commercial products, can be used which possess constituents which may contribute to different components. For example, a certain surfactant can be dissolved in an aprotic solvent, so that this product can contribute to the components (c1) and (c5) according to the invention. The combined products, as a mixture, can then generally be intensively mixed with one another and, if required, e.g. in the case of suspensions, can be milled.

Mixing can be carried out in a way known per se, e.g. by homogenization using suitable apparatuses, such as KPG or magnetic stirrers.

In the compositions of the present invention, the ethoxylated 2-propylheptanol acts as adjuvant. Thus, a higher fungicidal action is observed as compared to compositions which lack such ethoxylated 2-propylheptanol. The adjuvant action results in particular in the following aspects during the application of one or more than one fungicidal triazole, if appropriate in combination with one or more additional active ingredients:

in comparison, higher activity of the fungicidal triazole for a given amount applied;
in comparison, smaller amount of the fungicidal triazole applied for a given action;
in comparison, stronger uptake of the fungicidal triazole by the organism to be treated, in particular a plant, especially via the leaf, and thus advantages in the postemergence procedure, in particular in the spray treatment of plants.

Thus, the present invention thus also relates to the use of the above defined ethoxylated 2-propylheptanol as adjuvant in the treatment of a plant with a fungicidal triazole, i.e. for improving the efficacy of the triazole especially through better uptake of the triazole by the plant and in particular by the leafs of the plant.

As disclosed herein, the fungicidal triazoles and ethoxylated 2-propylheptanols may, in accordance with agricultural practice, be co-formulated to give a composition comprising both fungicidal triazole and ethoxylated 2-propylheptanol. Such a composition allows to simultaneously apply fungicidal triazole and ethoxylated 2-propylheptanol. However, the ethoxylated 2-propylheptanols may also be used as "stand alone" product, i.e., as such or, if appropriate, formulated in accordance with agricultural practice to give an additional composition. As "stand alone" product, the ethoxylated 2-propylheptanol will be co-applied, simultaneously or appropriately spaced in time, with the composition comprising the fungicidal triazole so that fungicidal triazole and ethoxylated 2-propylheptanols can act together.

In accordance with the use of the ethoxylated 2-propylheptanols as "stand alone" product, the combination according to the invention of fungicidal triazole and ethoxylated 2-propylheptanol can also be provided in the form of a kit. Such a kit comprises at least two containers. One container comprises at least one fungicidal triazole, if appropriate formulated as composition with suitable auxiliaries. An additional container comprises at least one ethoxylated 2-propylheptanol, if appropriate formulated as composition with suitable auxiliaries.

The use according to the invention relates to a number of different application possibilities which are directed in particular toward plant cultivation, agriculture and horticulture. The fungicidal triazoles are useful in particular as fungicides and are thus used for the control of a broad spectrum of phytopathogenic fungi, in particular from the classes of the Ascomycetes, Basidiomycetes, Phycomycetes and Deuteromycetes.

The present invention therefore also relates to methods, in accordance with the above intended purposes, for protecting a plant against a harmful fungus. This includes the treatment of plants which are infected by one or more harmful fungi or the treatment of plants for which infection by harmful fungi is feared and therefore would wish to be avoided. The methods comprise the application of a suitable amount of active ingredient and ethoxylated 2-propylheptanol.

The plants to be treated are principally plants or plant parts. The treatment is carried out such that an effective amount, in particular a fungicidally effective amount (amount applied), of the combination of active ingredient and ethoxylated 2-propylheptanol is allowed to act on the target plant or plant part. Application can be carried out before or after infection by the harmful fungi.

Advantages are achieved in particular in the control of a multitude of fungi (in particular rust, blights, leafspots, and mildews) on various cultivated plants, such as row crops (including but not limited to soybeans, sugarbeets, corn, wheat, cotton and peanuts), vegetable crops (including but not limited to tomatoes, potatoes and cucurbits), fruit crops (including but not limited to apples, peaches, grapes and turf) and ornamental plants.

They are especially suitable for controlling the following plant diseases:

*Alternaria* species on vegetables, rapeseed, sugar beet and fruit and rice,
*Aphanomyces* species on sugar beet and vegetables,
*Bipolaris* and *Drechslera* species on corn, cereals, rice and lawns,
*Blumeria graminis* (powdery mildew) on cereals,
*Botrytis cinerea* (gray mold) on strawberries, vegetables, flowers and grape vines,
*Bremia lactucae* on lettuce,
*Cercospora* species on corn, soybeans, rice and sugar beet,
*Cochliobolus* species on corn, cereals, rice (e.g., *Cochliobolus sativus* on cereals
*Cochliobolus miyabeanus* on rice),
*Colletotricum* species on soybeans and cotton,
*Exserohilum* species on corn,
*Erysiphe cichoracearum* and *Sphaerotheca fuliginea* on cucurbits,
*Fusarium* and *Verticillium* species on various plants,
*Gaeumanomyces graminis* on cereals,
*Gibberella* species on cereals and rice (e.g., *Gibberella fujikuroi* on rice),
Grain staining complex on rice,
*Helminthosporium* species on corn and rice,
*Michrodochium nivale* on cereals,
*Mycosphaerella* species on cereals, bananas and peanuts,
*Phakopsora pachyrhizi* and *Phakopsora meibomiae* on soybeans,
*Phomopsis* species on soybeans and sunflowers,
*Phytophthora infestans* on potatoes and tomatoes,
*Plasmopara viticola* on grapevines,
*Podosphaera leucotricha* on apples,
*Pseudocercosporella herpotrichoides* on cereals,
*Pseudoperonospora* species on hops and cucurbits,
*Puccinia* species on cereals and corn,
*Pyrenophora* species on cereals,
*Pyricularia oryzae, Corticium sasakii, Sarocladium oryzae, S. attenuatum, Entyloma oryzae* on rice,
*Pyricularia grisea* on lawns and cereals,
*Pythium* spp. on lawns, rice, corn, cotton, rapeseed, sunflowers, sugar beet, vegetables and other plants,
*Rhizoctonia* species on cotton, rice, potatoes, lawns, corn, rapeseed, potatoes, sugar beet, vegetables and other plants,
*Sclerotinia* species on rapeseed and sunflowers,
*Septoria tritici* and *Stagonospora nodorum* on wheat,
*Erysiphe* (syn. Uncinula) necator on grapevines,
*Setospaeria* species on corn and lawns,
*Sphacelotheca reilinia* on corn,
*Thievaliopsis* species on soybeans and cotton,
*Tilletia* species on cereals,
*Ustilago* species on cereals, corn and sugar beet, and
*Venturia* species (scab) on apples and pears.

The effective application thereto is within the scope of a person skilled in the art.

Particular advantages are especially in the control of the following phytopathogenic fungi: soybean rust (*Phakopsora meibomiae* and, in particular, *Phakopsora pachyrhizi*).

In principle, the amount of fungicidal triazole applied can be greatly varied as a result of high plant tolerance. Typically, the amounts applied according to the invention are, for the fungicidal triazoles, generally 0.001 to 2.5 kg/ha, preferably 0.005 to 2 kg/ha, in particular 0.01 to 1.0 kg/ha, and, for the ethoxylated 2-propylheptanols, generally 0.001 to 25 kg/ha, preferably 0.05 to 2 kg/ha, in particular 0.1 to 1 kg/ha.

The ratio of the amounts applied of ethoxylated 2-propylheptanols to fungicidal triazoles generally ranges from 0.5:1 to 100:1, preferably 1:1 to 50:1, in particular 1:1 to 20:1. According to a particular aspect, the amounts applied of ethoxylated 2-propylheptanols are greater than amounts applied of fungicidal triazoles.

The fungicidal triazoles, ethoxylated 2-propylheptanols and/or compositions comprsing triazole and/or ethoxylated 2-propylheptanol can be applied in a way known per se, e.g. by spraying, atomizing, dusting, broadcasting or watering. For this, it may be necessary, first, to prepare a spray mixture, which is then applied, e.g. with a mobile sprayer using nozzles which distribute as finely as possible. The usual devices and working techniques for this are known to a person skilled in the art.

Sprayable mixtures normally comprise 0.0001 to 10, preferably 0.001 to 5 and in particular 0.002 to 2.0% by weight of fungicidal triazole. For the preparation of a conventional spray mixture, for example 0.2 to 5.0, preferably 0.3 to 3.0 and in particular 0.35 to 2.0 l of a composition according to the invention comprising the fungicidal triazole(s) can be diluted with water to 10 to 2000 l, preferably 50 to 1500 l and in particular 100 to 1000 l. If appropriate, 0.1% by weight to 5% by weight (based on the spray mixture) of additional auxiliaries can be added to the spray mixture. Mention may be made, as examples of materials for such auxiliaries, of starch and starch derivatives, e.g. a starch comprising carboxyl and sulfo groups (Nu Film from Union Carbide Corp.), and spreaders and extenders, such as Vapor Guard from Miller Chemical & Fertilizer Corp.

Application of a fungicidal triazole may induce chlorosis. Also, chlorosis appears to be related to triazole uptake and thus agents that promote triazole uptake would be expected to enhance chlorosis and thus chlorosis-related damage.

Chlorosis is defined as a disease condition of green plants seen as yellowing or whitening of normally green plant tissue because of a decreased amount of chlorophyll. According to the invention, chlorosis is meant to refer to triazole-induced chlorosis and especially chlorosis at day 7, 14, 21, 28 or 35 after treatment.

Surprisingly, it has been found that the use of ethoxylated 2-propylheptanol having a mole average degree of ethoxylation from 7.5 to 8.5, in accordance with the present invention, reduces fungicidal triazole-induced chlorosis. Thus, less fungicidal triazole-induced chlorosis is observed as compared to fungicidal triazole-related compositions and uses which
    lack or do not involve such ethoxylated 2-propylheptanol and either
        comprise or involve 2-propyheptanol having a different mole average degree of ethoxylation, i.e. a mole average degree of ethoxylation of less than 7.5 or higher than 8.5, or
        comprise or involve one or more than one alkoxylated alcohol other than 2-propylheptanol.

Thus, according to the present invention ethoxylated 2-propylheptanol having a mole average degree of ethoxylation from 7.5 to 8.5 may be used as a safener. A safener is generally a substance added to a pesticide formulation to eliminate or reduce phytotoxic effects of the pesticide to certain crops. The safener action of the ethoxylated 2-propylheptanols manifests itself in that the induction of plant chlorosis by the fungicidal triazole is absent or not as pronounced.

The reduction of fungicidal triazole-induced chlorosis according to the present invention is of particular importance if the treatment comprises applying the fungicidal triazole and the ethoxylated 2-propylheptanol to a part of the plant that is susceptible to chlorosis. Parts of plants that are susceptible to chlorosis include in particular leafs and stems.

Within the scope of the present description, amounts generally refer in respect of the total weight of the composition, unless otherwise specified. In accordance with the invention, the expression "essentially" generally describes a percentage ratio of at least 90%, preferably of at least 95% and in particular of at least 98%.

The invention is more fully illustrated by the following example:

EXAMPLE 1

Chlorosis in Soybeans Treated with Metconazole a) 2-Propylheptanol×8 EO Vs. $C_9$-$C_{11}$ Alcohol×6 EO Formulation A was prepared using $C_9$-$C_{11}$ alcohol×6 EO (60%), diethylene glycol (31%), and metconazole (9%).
Formulation B was prepared using 2-propylheptanol×8 EO (60%), diethylene glycol (31%), and metconazole (9%).
Each formulation was mixed with water, and sprayed onto soybeans using an equivalent of 100 liters per hectare.
There were 2 application rates used, 50 g ai metconazole/ha and 100 g ai metconazole/ha of the formulations.
The results can be summarized as follows:

| Formulation | Metconazole | Adjuvant | Chlorosis (% leaf area) 21 DAT | 28 DAT |
|---|---|---|---|---|
| Formulation A | 50 g/ha | $C_9$-$C_{11}$ alcohol × 6 EO | 12 | 10 |
| Formulation B | 50 g/ha | 2-Propylheptanol × 8 EO | 3 | 0 |
| Formulation A | 100 g/ha | $C_9$-$C_{11}$ alcohol × 6 EO | 22 | 23 |
| Formulation B | 100 g/ha | 2-Propylheptanol × 8 EO | 7 | 12 | b) Varying the Degree of Ethoxylation

Formulation B was prepared using 2-propylheptanol×8 EO (60%), diethylene glycol (31%), and metconazole (9%).
Formulation C was prepared using 2-propylheptanol×6 EO (60%), diethylene glycol (31%), and metconazole (9%).
Formulation D was prepared using 2-propylheptanol×10 EO (60%), diethylene glycol (31%), and metconazole (9%).
Each formulation was mixed with water, and sprayed onto sobeans using an equivalent of 100 liters per hectare.
There were 2 application rates used, 50 g ai metconazole/ha and 100 ai metconazole/ha of the formulations.
The results can be summarized as follows:

| Formulation | Metconazole | Mole average degree of ethoxylation of 2-Propylheptanol | Chlorosis (% leaf area) 21 DAT | 28 DAT |
|---|---|---|---|---|
| Formulation C | 50 g/ha | 6 | 10 | 22 |
| Formulation C | 100 g/ha | 6 | 18 | 20 |
| Formulation B | 50 g/ha | 8 | 7 | 8 |
| Formulation B | 100 g/ha | 8 | 5 | 10 |
| Formulation D | 50 g/ha | 10 | 11 | 10 |
| Formulation D | 100 g/ha | 10 | 30 | 22 | c) Varying Concentration of 2-Propylheptanol×8 EO

Formulation B was prepared using 2-propylheptanol×8 EO (60%), diethylene glycol (31%), and metconazole (9%).
Formulation E was prepared using diethylene glycol (91%), and metconazole (9%).
Formulation F was prepared using 2-propylheptanol×8 EO (10%), diethylene glycol (81%), and metconazole (9%).
Formulation G was prepared using 2-propylheptanol×8 EO (20%), diethylene glycol (71%), and metconazole (9%).
Formulation H was prepared using 2-propylheptanol×8 EO (40%), diethylene glycol (51%), and metconazole (9%).
Each formulation was mixed with water, and sprayed onto soybeans using an equivalent of 100 liters per hectare.
There were 2 application rates used, 50 g ai metconazole/ha and 100 g ai metconazole/ha of the formulations.
The results can be summarized as follows:

| Formulation | Metconazole | 2-Propylheptanol × 8 EO | Chlorosis (% leaf area) 21 DAT | 28 DAT |
|---|---|---|---|---|
| | Untreated | | 0 | 0 |
| Formulation E | 50 g/ha | 0 g/ha | 8 | 7 |
| Formulation F | 50 g/ha | 55.5 g/ha | 27 | 18 |
| Formulation G | 50 g/ha | 111 g/ha | 7 | 8 |
| Formulation H | 50 g/ha | 222 | 2 | 12 |
| Formulation B | 50 g/ha | 306 | 4 | 0 |
| Formulation E | 100 g/ha | 0 g/ha | 17 | 18 |
| Formulation F | 100 g/ha | 111 g/ha | 35 | 16 |
| Formulation G | 100 g/ha | 222 g/ha | 5 | 10 |

-continued

| Formulation | Metconazole | 2-Propylheptanol × 8 EO | Chlorosis (% leaf area) 21 DAT | 28 DAT |
|---|---|---|---|---|
| Formulation H | 100 g/ha | 444 | 10 | 12 |
| Formulation B | 100 g/ha | 611 | 7 | 12 |

We claim:

1. Composition comprising
   (a1) a fungicidal triazole; and
   (b1) ethoxylated 2-propylheptanol having a mole average degree of ethoxylation from 7.5 to 8.5, wherein at least 70% by weight of the ethoxylated 2-propylheptanol has an ethoxylation number between 7.5 and 8.5.

2. Composition according to claim 1, wherein the degree of ethoxylation is about 8.

3. Composition according to claim 1, wherein the ethoxylated 2-propylheptanol comprises at least 50% by weight, at least 60% by weight, at least 70% by weight, at least 80% by weight, at least 90% by weight or at least 95% by weight of ethoxylated 2-propylheptanol of the formula (I)

R—O—(C$_2$H$_4$O)$_x$H    (I)

wherein R is 2-propylheptyl and x is 8.

4. Composition according to claim 1, wherein the triazole is selected from the group consisting of metconazole, triadimenol, triadimefon, cyproconazole, tebuconazole, uniconazole, paclobutrazol, ipconazole, prothioconazole, tetraconazole, epoxiconazole, propiconazole, triticonazole, difenoconazole, fenbuconazole and flusilazole, and agriculturally utilizable salts thereof.

5. Composition according to claim 1, wherein the triazole is metconazole or an agriculturally utilizable salt thereof.

6. Composition according to claim 1, wherein component (a1) amounts to more than 1% by weight based on the total weight of the composition.

7. Composition according to claim 1, wherein component (a1) amounts to more than 2.5% by weight based on the total weight of the composition.

8. Composition according to claim 1, wherein component (b1) amounts to more than 10% by weight based on the total weight of the composition.

9. Composition according to claim 1, wherein component (b1) amounts to more than 20% by weight based on the total weight of the composition.

10. Composition according to claim 1, which is a dispersible concentrate (DC).

11. A kit with at least two containers, in which
    (a) a first container comprises a fungicidal triazole; and
    (b) a second container comprises ethoxylated 2-propylheptanol having a mole average degree of ethoxylation from 7.5 to 8.5, wherein at least 70% by weight of the ethoxylated 2-propylheptanol has an ethoxylation number between 7.5 and 8.5.

12. Method of protecting a plant against a harmful fungus, which comprises treating the plant with (a1) a fungicidal triazole and (b1) ethoxylated 2-propylheptanol having a mole average degree of ethoxylation from 7.5 to 8.5, wherein at least 70% by weight of the ethoxylated 2-propylheptanol has an ethoxylation number between 7.5 and 8.5.

13. Method according to claim 12, wherein the plant is selected from the group consisting of row crops, vegetable crops, fruit crops, and ornamental plants.

14. Method according to claim 12, wherein the harmful fungus is selected from rust, blights, leafspots, and mildews.

15. Method according to claim 12, wherein the treatment is a post-emergence treatment.

16. Method according to claim 12, wherein the treatment is a spray treatment.

17. Method according to claim 12, wherein the treatment comprises applying the triazole and the ethoxylated 2-propylheptanol to a part of the plant that is susceptible to chlorosis.

18. Method according to claim 17, wherein the part of the plant that is susceptible to chlorosis is a leaf.

19. Method for reducing fungicidal triazole-induced chlorosis of a plant, which comprises treating the plant with ethoxylated 2-propylheptanol having a mole average degree of ethoxylation from 7.5 to 8.5, wherein at least 70% by weight of the ethoxylated 2-propylheptanol has an ethoxylation number between 7.5 and 8.5.

20. The method according to claim 19, wherein chlorosis is induced by the triazole uptake after application.

21. Composition comprising
    (a1) a fungicidal triazole; and
    (b1) ethoxylated 2-propylheptanol having a mole average degree of ethoxylation from 7.5 to 8.5, wherein about 70% by weight of the ethoxylated 2-propylheptanol has an ethoxylation number between 7.5 and 8.5.

22. A kit with at least two containers, in which
    (a) a first container comprises a fungicidal triazole; and
    (b) a second container comprises ethoxylated 2-propylheptanol having a mole average degree of ethoxylation from 7.5 to 8.5, wherein about 70% by weight of the ethoxylated 2-propylheptanol has an ethoxylation number between 7.5 and 8.5.

23. Method of protecting a plant against a harmful fungus, which comprises treating the plant with (a1) a fungicidal triazole and (b1) ethoxylated 2-propylheptanol having a mole average degree of ethoxylation from 7.5 to 8.5, wherein about 70% by weight of the-ethoxylated 2-propylheptanol has an ethoxylation number between 7.5 and 8.5.

24. Method for reducing fungicidal triazole-induced chlorosis of a plant, which comprises treating the plant with ethoxylated 2-propylheptanol having a mole average degree of ethoxylation from 7.5 to 8.5, wherein about 70% by weight of the ethoxylated 2-propylheptanol has an ethoxylation number between 7.5 and 8.5.

* * * * *